(12) United States Patent
Bassett et al.

(10) Patent No.: US 6,250,922 B1
(45) Date of Patent: *Jun. 26, 2001

(54) TWO-PIECE DENTAL ABUTMENT WITH REMOVABLE CUFF

(75) Inventors: Jeffrey A. Bassett, Vista; Peter S. Armstrong, San Diego; Carl W. Pettersen, San Diego; Thomas H. Day, San Diego, all of CA (US); Philip S. Lyren, Houston, TX (US)

(73) Assignee: Sulzer Dental Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/429,816

(22) Filed: Oct. 29, 1999

Related U.S. Application Data (63) Continuation-in-part of application No. 09/126,511, filed on Jul. 30, 1998, now Pat. No. 6,012,923.

(51) Int. Cl.⁷ ........................................... A61C 8/00

(52) U.S. Cl. ........................................... 433/172; 433/173

(58) Field of Search ................................... 433/172, 173, 433/174, 175, 201.1

(56) References Cited

U.S. PATENT DOCUMENTS

| | | | |
|---|---|---|---|
| D. 209,508 | 12/1967 | Macker et al. .................... | D26/5 |
| D. 273,984 | 5/1984 | Vlock .................................. | D24/10 |
| D. 281,904 | 12/1985 | Linkow et al. .................... | D24/33 |
| D. 290,506 | 6/1987 | Weissman .......................... | D24/10 |
| D. 290,507 | 6/1987 | Weissman .......................... | D24/10 |
| D. 292,124 | 9/1987 | Roden et al. ...................... | D24/16 |
| D. 292,125 | 9/1987 | Roden et al. ...................... | D24/16 |
| D. 294,295 | 2/1988 | Branemark ........................ | D24/33 |
| D. 296,362 | 6/1988 | Branemark ........................ | D24/33 |
| D. 303,709 | 9/1989 | Roden et al. ...................... | D24/16 |
| D. 303,836 | 10/1989 | Roden et al. ...................... | D24/16 |
| D. 314,821 | 2/1991 | Miller ................................ | D24/10 |
| D. 314,822 | 2/1991 | Miller ................................ | D24/10 |
| D. 317,200 | 5/1991 | Jorneus ............................. | D24/156 |
| D. 319,500 | 8/1991 | Soderberg ......................... | D24/156 |
| D. 321,560 | 11/1991 | Miller ............................... | D24/156 |
| D. 324,731 | 3/1992 | Sullivan ........................... | D24/156 |
| D. 325,085 | 3/1992 | Branemark et al. ............... | D24/156 |
| D. 330,767 | 11/1992 | Jorneus ............................. | D24/156 |
| D. 338,959 | 8/1993 | Loof et al. ........................ | D24/156 |
| D. 339,420 | 9/1993 | Nordin .............................. | D24/156 |
| D. 342,314 | 12/1993 | Miller ............................... | D24/156 |
| D. 353,674 | 12/1994 | Jorneus ............................. | D24/156 |
| D. 355,972 | 2/1995 | Broberg et al. ................... | D24/156 |
| D. 356,868 | 3/1995 | Broberg et al. ................... | D24/156 |
| D. 356,869 | 3/1995 | Holmen et al. ................... | D24/156 |
| D. 358,212 | 5/1995 | Sullivan ........................... | D24/156 |
| D. 362,720 | 9/1995 | Holmen et al. ................... | D24/155 |
| D. 366,115 | 1/1996 | Sullivan ........................... | D24/156 |
| D. 370,978 | 6/1996 | Broberg et al. ................... | D24/156 |
| D. 374,079 | 9/1996 | Broberg ............................ | D24/156 |
| D. 374,080 | 9/1996 | Broberg ............................ | D24/156 |
| D. 380,047 | 6/1997 | Gelb ................................. | D24/156 |
| 3,082,525 | 3/1963 | Christensen ...................... | 32/2 |
| 3,458,936 | 8/1969 | Schulz et al. .................... | 32/71 |
| 4,180,910 | 1/1980 | Straumann et al. .............. | 433/173 |
| 4,279,598 | 7/1981 | Scheicher ........................ | 433/173 |
| 4,552,532 | 11/1985 | Mozsary ......................... | 433/173 |
| 4,790,753 | 12/1988 | Fradera ........................... | 433/174 |
| 4,801,264 | 1/1989 | Weissman ....................... | 433/74 |
| 4,915,628 | 4/1990 | Linkow et al. ................. | 433/173 |
| 5,087,199 | 2/1992 | Lazarof .......................... | 433/173 |
| 5,100,323 | * 3/1992 | Friedman et al. .............. | 433/173 |
| 5,116,225 | * 5/1992 | Riera .............................. | 433/173 |
| 5,297,963 | * 3/1994 | Dafatry .......................... | 433/172 |
| 5,344,457 | * 9/1994 | Pilliar et al. ................... | 433/174 |

(List continued on next page.)

Primary Examiner—John J. Wilson
(74) Attorney, Agent, or Firm—Philip S. Lyren (57) ABSTRACT

A two-piece dental abutment having a cuff portion that is removable from a upper portion. The upper portion engages and retains the cuff portion during abutment placement.

41 Claims, 11 Drawing Sheets

U.S. PATENT DOCUMENTS

| | | | |
|---|---|---|---|
| 5,407,359 | * | 4/1995 | Balfour et al. ............... 433/173 |
| 5,421,722 | | 6/1995 | Stemmann ................... 433/189 |
| 5,449,291 | * | 9/1995 | Lueschen et al. ............ 433/173 |
| 5,527,182 | * | 6/1996 | Willoughby ................. 433/172 |
| 5,564,921 | * | 10/1996 | Marlin ......................... 433/172 |
| 5,628,630 | | 5/1997 | Misch et al. ................. 433/174 |
| 5,636,989 | | 6/1997 | Somborac et al. ........... 433/173 |
| 5,636,990 | | 6/1997 | Stemmann ................... 433/189 |
| 5,639,237 | | 6/1997 | Fontenot ...................... 433/173 |
| 5,642,996 | | 7/1997 | Mochida et al. ............. 433/174 |
| 5,651,675 | | 7/1997 | Singer ......................... 433/172 |
| 5,658,147 | | 8/1997 | Phimmasone ............... 433/213 |
| 5,660,545 | | 8/1997 | Bailey et al. ................ 433/173 |
| 5,662,473 | | 9/1997 | Rassoli et al. .............. 433/172 |
| 5,662,475 | | 9/1997 | Mena ........................... 433/172 |
| 5,662,476 | | 9/1997 | Ingber et al. ................ 433/213 |
| 5,667,384 | | 9/1997 | Sutter et al. ................. 433/172 |
| 5,674,071 | | 10/1997 | Beaty et al. ................. 433/172 |
| 5,674,072 | | 10/1997 | Moser et al. ................ 433/173 |
| 5,674,073 | | 10/1997 | Ingber et al. ................ 433/213 |
| 5,678,995 | | 10/1997 | Kirsch et al. ............... 433/169 |
| 5,678,997 | | 10/1997 | De Buck ..................... 433/177 |
| 5,678,998 | | 10/1997 | Honkura et al. ............. 433/189 |
| 5,681,167 | * | 10/1997 | Lazarof ....................... 433/174 |
| 5,683,249 | | 11/1997 | Ibsen et al. .................. 433/201.1 |
| 5,685,714 | | 11/1997 | Beaty et al. ................. 433/172 |
| 5,685,715 | | 11/1997 | Beaty et al. ................. 433/173 |
| 5,690,843 | | 11/1997 | Schmitt et al. .............. 219/63.17 |

* cited by examiner (PRIOR ART)
FIG. 1

TWO-PIECE DENTAL ABUTMENT WITH REMOVABLE CUFF

This is a continuation-in-part of U.S. application Ser. No. 09/126,511, filed on Jul. 30, 1998, now U.S. Pat. No. 6,012,923 by Jeffrey A. Bassett, Peter S. Armstrong, Carl W. Pettersen, and Philip S. Lyren, entitled TWO-PIECE DENTAL ABUTMENT WITH REMOVABLE CUFF.

BACKGROUND OF THE INVENTION

During a typical dental implantation procedure, the tissue surrounding the jawbone is cut to expose the implantation site. A hole is drilled into the bone, and a dental implant is positioned into this hole. The tissue is then sutured, and the implant is left in the bone for several months as healing and osseointegration occur. During this healing period, a prosthesis or artificial tooth is custom made to fit in the patient's mouth. During a second surgical procedure, the tissue surrounding the implantation site is again cut. The prosthesis is then connected to the end of the implant.

Typically, a dental abutment is located between the implant and prosthesis. The abutment serves several functions but generally provides a structure for extending the implant above the gum-line. One end of the abutment connects to the implant while a second end of the abutment connects to the prosthesis. Typically, a screw holds the abutment to the implant, and either another screw or cement holds the abutment to the prosthesis.

Abutments may have numerous configurations, but generally they have a straight or angled cylindrical configuration. U.S. Pat. No. 5,069,622 entitled "Spacer" to Rangert et al. illustrates an angled abutment, shown in FIG. 1 (prior art).

Figure 1:
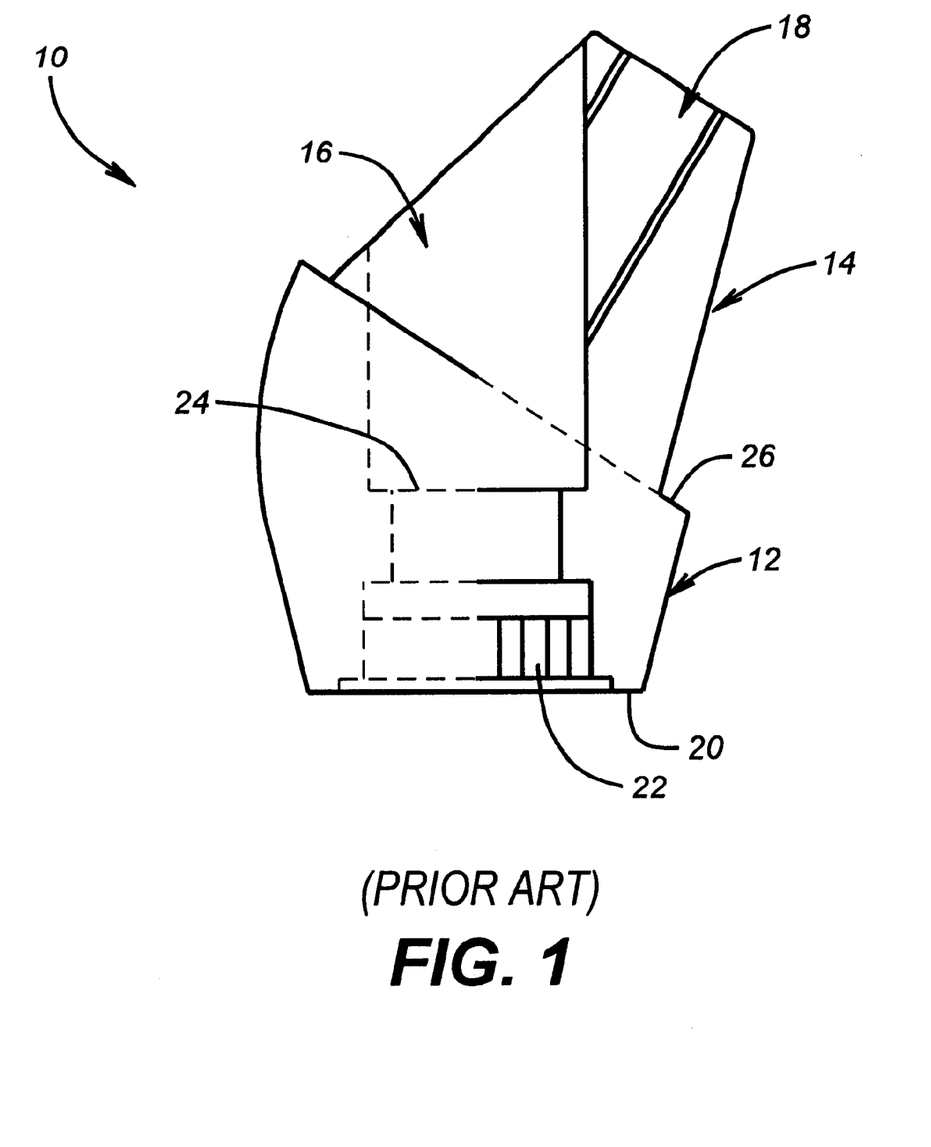
FIG. 1 is an angled dental abutment known in the prior art.

FIG. 1 shows a one-piece angled abutment at 10. This abutment includes a conical base portion 12 and a conical upper portion 14. These two portions are not removable from one another and are formed together to make a unitary member.

A first bore 16 extends downwardly through both the base and upper portions, and a second threaded bore 18 extends through the upper portion. The base portion 12 has a conical shape and includes a bottom surface 20 that abuts against the end of an implant (not shown). An interior portion of the bottom of bore 16 has a non-cylindrical shape 22 to provide anti-rotational engagement between the abutment and implant. A screw (not shown) passes into bore 16, abuts against a ledge 24, and holds the abutment to the implant.

The upper portion 14 tapers away from the base portion at a preselected angle, preferably between 25° and 40°. The prosthesis fits around the upper portion and abuts against a ledge 26 at the top of the base portion. A screw (not shown) passes into a threaded bore 18 to hold the prosthesis to the abutment.

One important disadvantage with prior straight and angled abutments is that the base portion cannot be removed from the upper portion. In some instances, however, the base portion needs to be removed or replaced. For example, the tissue surrounding the base of the abutment tends to recede over time. As this tissue recedes, more and more of the abutment is visible in the patient's mouth. The abutment, usually made of the metal titanium, has an unappealing appearance and disrupts the aesthetic quality of the prosthesis.

As another disadvantage, prior abutments have base and upper portions made from the same material. Generally, the abutments are formed as a solid piece of titanium or other suitable material. Numerous advantages could be realized if the base portion were formed from one material while the upper portion were formed from another material.

As another disadvantage, prior abutments are not well suited to have the base portion colored or coated while leaving the upper portion uncolored or uncoated.

The present invention solves the problems discussed above with prior dental abutments and provides further advantages.

SUMMARY OF THE INVENTION

The present invention is directed toward a multi-piece abutment having a cuff portion that can be removed from an upper portion. The cuff and the upper portion are two separate pieces that connect together to form the abutment. The upper portion has a base that connects to the top of the cuff. Once the upper portion and cuff are connected, the abutment is used in a conventional fashion with the cuff attaching to the implant and the upper portion attaching to the prosthesis.

The present invention has numerous advantages. For instance, after the prosthesis is connected to the abutment and placed in the mouth of the patient, the abutment may be disassembled into two separate pieces. In some circumstances, the cuff of the abutment may need to be replaced with a new or different cuff. This replacement cuff, for example, may be shorter or wider than the original cuff to compensate for receding tissue around the prosthesis.

As another advantage, the upper portion and the cuff may be made from different materials. Various combinations of materials may be used to meet particular needs of the patient. For example, the cuff may be formed from a material having good aesthetic qualities, especially where the abutment is likely to be exposed, and the upper portion may be formed from a material having a high strength, especially where the abutment requires added strength. The upper portion, for instance, could be made from titanium while the cuff is made from a gold alloy, polymer, or ceramic.

As another advantage, the cuff may be colored or have a coating, such as porcelain. This coloring or coating could be separate from the upper portion and would enhance the aesthetics of the abutment.

The invention, accordingly, comprises the apparatus and method possessing the construction, combination of elements, and arrangement of parts that are exemplified in the following detailed description. For a fuller understanding of the nature and objects of the invention, reference should be made to the following detailed description taken in connection with the accompanying drawings.

DETAILED DESCRIPTION OF THE PREFERRED EMBODIMENT

Figures 2, 3:
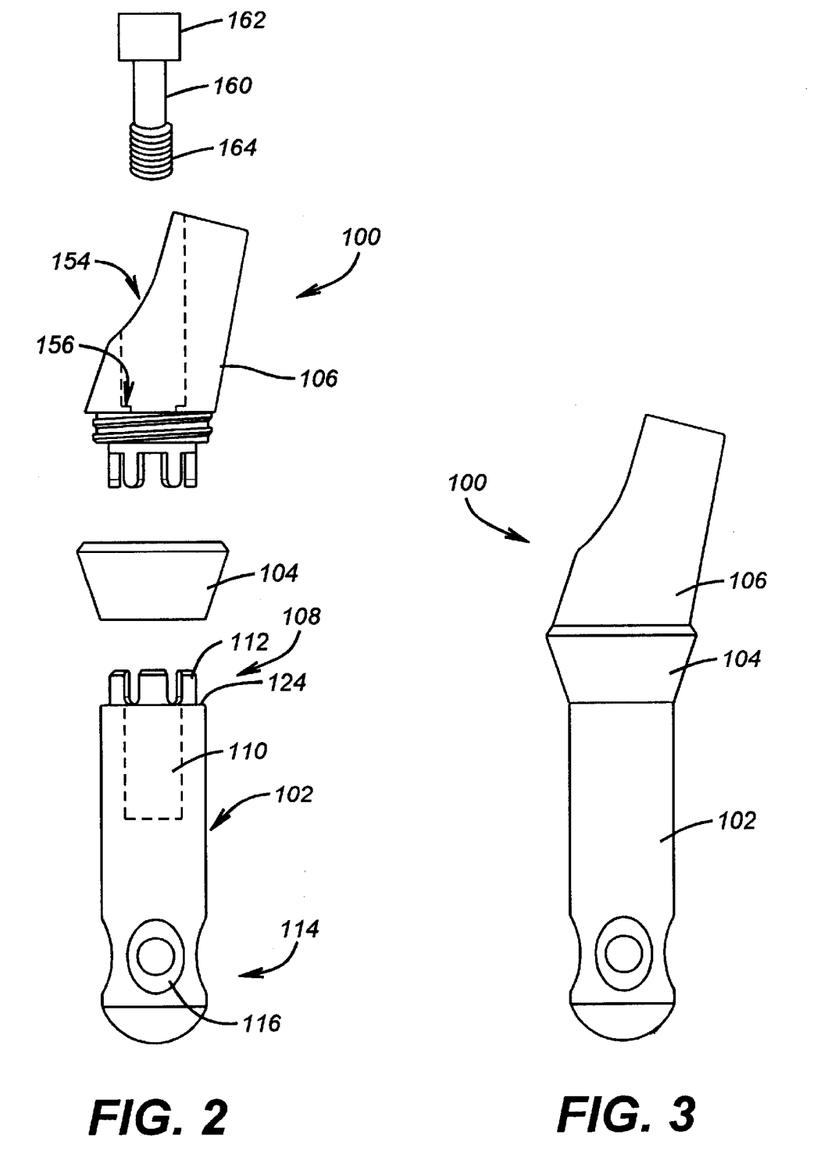
FIG. 2 is an exploded view of a dental implant and a two-piece dental abutment according to the present invention.
FIG. 3 is a side-view of the abutment and implant of FIG. 2 connected together.

FIGS. 2 and 3 show a multi-piece dental abutment 100 connecting to an implant 102. The abutment consists of two separate pieces, a cuff 104 and an upper portion 106. The cuff and upper portion may be connected together and attached to the implant.

Implant 102 has a coronal end 108 with a threaded bore 110 and a plurality of upwardly extending tines 112. A distal end 114 of the implant shows a bore 116 for aiding integration between the implant and bone. The implant may be any one of various dental implants known to those skilled in the art, such as a TWIST™ implant manufactured by Sulzer Calcitek, Inc. of Carlsbad, Calif.

Figure 4A:
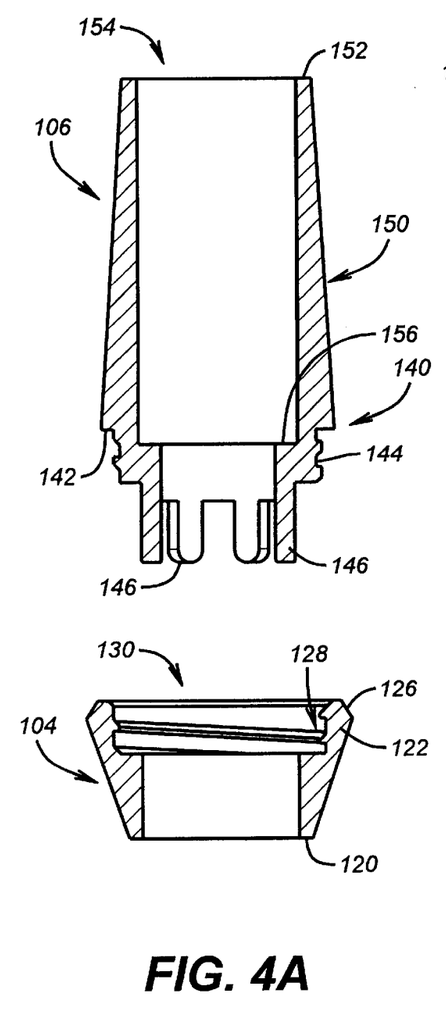
FIG. 4A is a cross sectional view of the abutment having a straight upper portion.
Figure 4B:
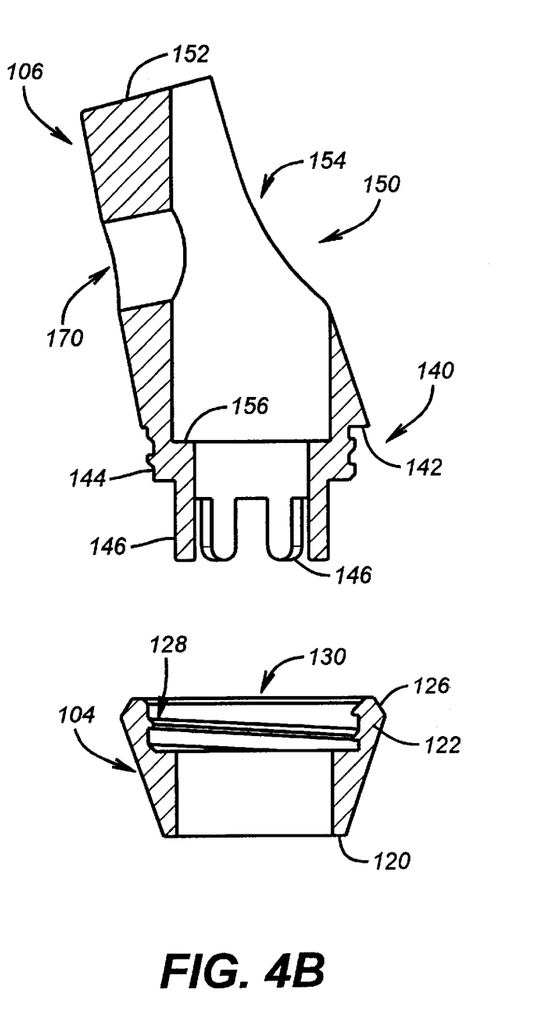
FIG. 4B is a cross sectional view of the abutment having a conical upper portion.

Turning also FIGS. 4A and 4B, two different embodiments for the abutment 100 are shown in greater detail. Cuff 104 has a conical cross section that tapers from a support surface 120 to a top portion 122. This cross section could also have a more straight cylindrical configuration. Surface 120 abuts against a ledge 124 at the coronal end of the implant. Top portion 122 includes a tapered shoulder 126 that abuts against the bottom end of a prosthesis (not shown). The top portion also includes a threaded section 128. These threads extend along the interior wall formed from a cylindrical bore 130 that extends through the cuff.

The upper portion 106 has a base portion generally denoted at 140. This base includes a lip 142 with an adjacent threaded section 144. A plurality of tines 146 extend downwardly to the end of the base. Threads 144 on the upper portion engage threads 128 on the cuff to connect the upper portion and cuff and form an assembled abutment. When the abutment is assembled, the tines 146 on the base extend into bore 130. These tines then engage with the tines 112 at the coronal end of the implant. Together, these two sets of tines provide anti-rotational engagement between the implant and the abutment.

The upper portion 106 also includes a top portion 150 that extends from lip 142 to an end surface 152. A cylindrical bore 154 extends from end 152 through the base 140. This bore aligns with the bore 130 in the cuff when the abutment is assembled. The bore 154 in the upper portion includes a shoulder 156.

As best shown in FIG. 2, a screw 160 passes into bore 154 in the upper portion until the head 162 of the screw abuts against shoulder 156. A threaded portion 164 of the screw fits into the coronal end of the implant to engage corresponding threads in bore 110. As shown in FIG. 3, the screw holds the assembled abutment to the implant.

FIGS. 4A and 4B show two different upper portions. In FIG. 4A, the upper portion 104 connects to the cuff to form a straight abutment. Typically, straight abutments have either a slightly tapering conical configuration (as shown in FIG. 4A) or a non-tapered or straight cylindrical configuration (not shown).

In FIG. 4B, the upper portion connects to the cuff to form an angled abutment. Typically, these abutments have either a tapering conical configuration (as shown in FIG. 4B) that angles with respect to the base or a non-tapered or straight cylindrical configuration (not shown) that angles with respect to the base. The angled abutments are available with angles ranging from about 5° to about 40°.

Abutments usually connect to the prosthesis with cement or a screw. FIG. 4A illustrates a cement retained connection. The prosthesis fits around the conical top portion 150, and cement is used to attach the prosthesis to the upper portion. FIG. 4B illustrates a screw retained connection. Here, the prosthesis also fits around the conical top portion 150, but a screw (not shown) passes through a bore in the prosthesis and into a threaded opening 170. This threaded opening is formed as a cylindrical bore that passes through the backside of the upper portion. This type of screw connection is known as a lingual screw connection.

The threaded opening, however, does not have to be located through the side of the upper portion as shown in FIG. 4B. Alternatively, this opening may be located through the top of the upper portion and extend through end 152.

The two piece abutment of the present invention has numerous advantages over prior abutments. First, even after the prosthesis has been placed on the abutment and in a patient's mouth, the cuff on the abutment may be easily and readily replaced with a new or even different cuff. In some instances, for example, the tissue surrounding the implant and prosthesis may recede over time. As this tissue recedes, the cuff portion of the abutment may become exposed. Since abutments are typically made of metal, such as titanium, the exposed portion of the cuff has an unwanted and unsightly aesthetic appearance in the mouth. With the present invention, however, the old cuff can be replaced with a new or different cuff to minimize the visible portions of the cuff. The new cuff, for example, may have a different size or be shaped differently such that no portion of the cuff is exposed. Alternatively, the old cuff may be replaced with one that is coated, colored, or painted to camouflage the abutment in the mouth.

Another important advantage of the present invention is that the cuff and upper portion of the abutment may be made of different materials. In the preferred embodiment, the upper portion is made from titanium, such as any one of various titanium alloys known to those skilled in the art. Making the upper portion from titanium provides the abutment with strength and biocompatibility.

The cuff may be made from several different possible materials, apart from titanium. The cuff, for example, may be made from steel or a precious metal alloy, such as gold, silver, or iridium. A cuff made from a gold alloy, for example, would have several advantages. Certain gold alloys enable the cuff to easily receive a porcelain coating favorable for aesthetic reasons. A gold cuff coated with porcelain also is less prone to scratch or otherwise show surface marks, as opposed to a titanium cuff. As another advantage, a gold cuff may be used with gold casting procedures, such as a casting procedure to create a custom geometry or anatomical profile around the cuff.

The cuff may be made from other materials suited for dental applications. Some of these materials include ceramics (such as aluminum oxide), polymers, composites, or materials having a coating that promotes tissue growth.

Figure 5:
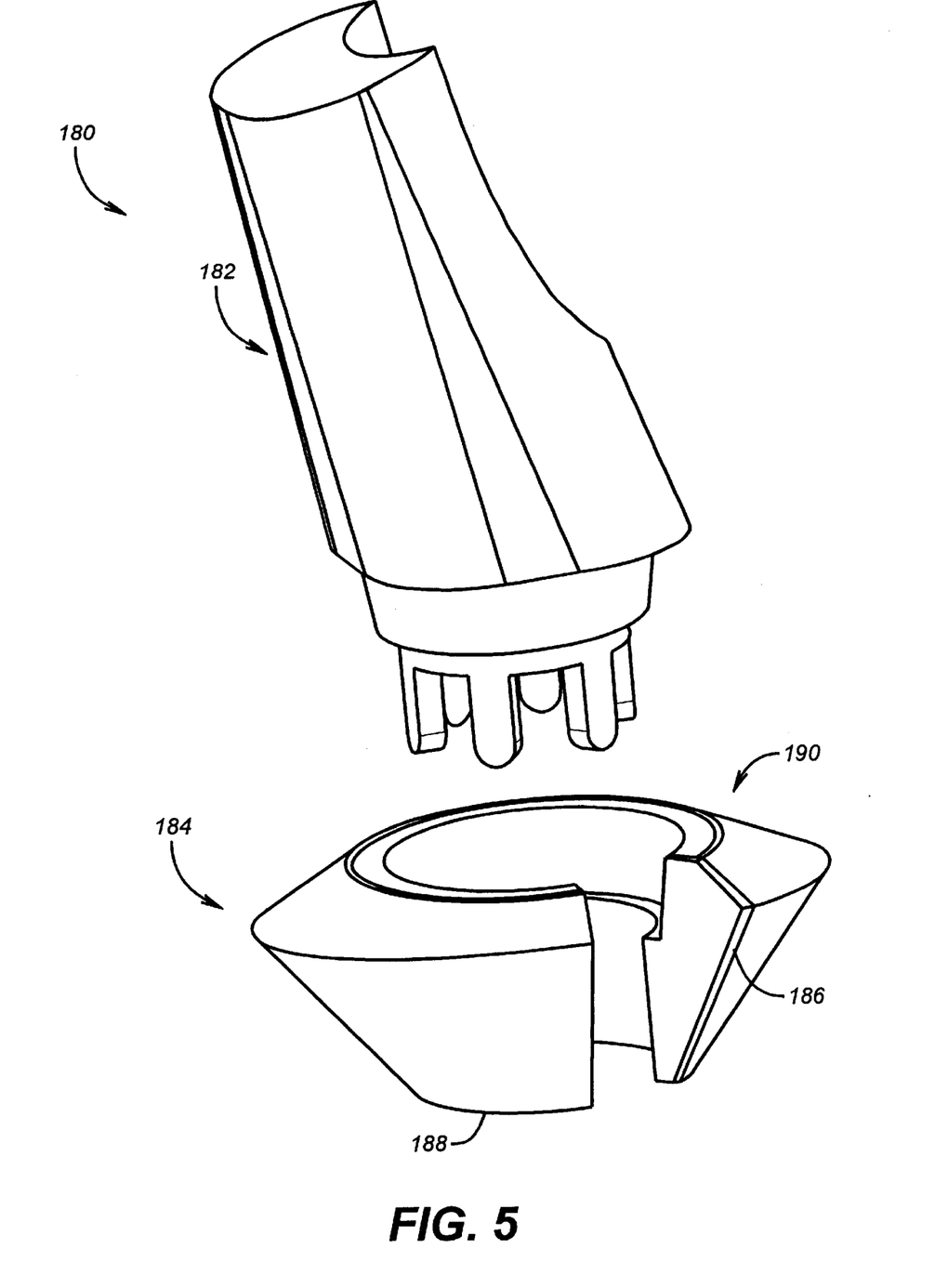
FIG. 5 is an exploded view of an alternate two-piece dental abutment.

FIG. 5 shows an abutment 180 illustrating some of the advantages of the present invention. In the figure, the upper portion 182 is made of a titanium alloy and has a configuration similar to the upper portion described in FIGS. 2 and 3. The cuff 184 is made from a gold alloy and has a thin porcelain coating 186 along the exterior surface. The cuff tapers from a support surface 188 toward top portion 190. This top portion, however, has an anatomical profile in the shape of an ellipse. This profile more closely resembles the shape of a natural tooth and, as such, encourages and promotes natural soft tissue growth around the cuff. Proper bio-aesthetics are also enhanced with this cuff.

Although FIG. 5 shows a specific embodiment, it will be appreciated that numerous other combinations with a separate cuff and upper portion are also within the scope of this invention. For example, the cuff could be made of a polymer or ceramic with an elliptical profile. Likewise, the geometry of the cuff could be changed to another anatomical profile, such as a tri-lobed configuration.

As noted, one important advantage of the present invention is the ability to change cuffs after the prosthesis is attached in the patient's mouth. The method for changing the cuff is now discussed in more detail.

Figures 6, 7:
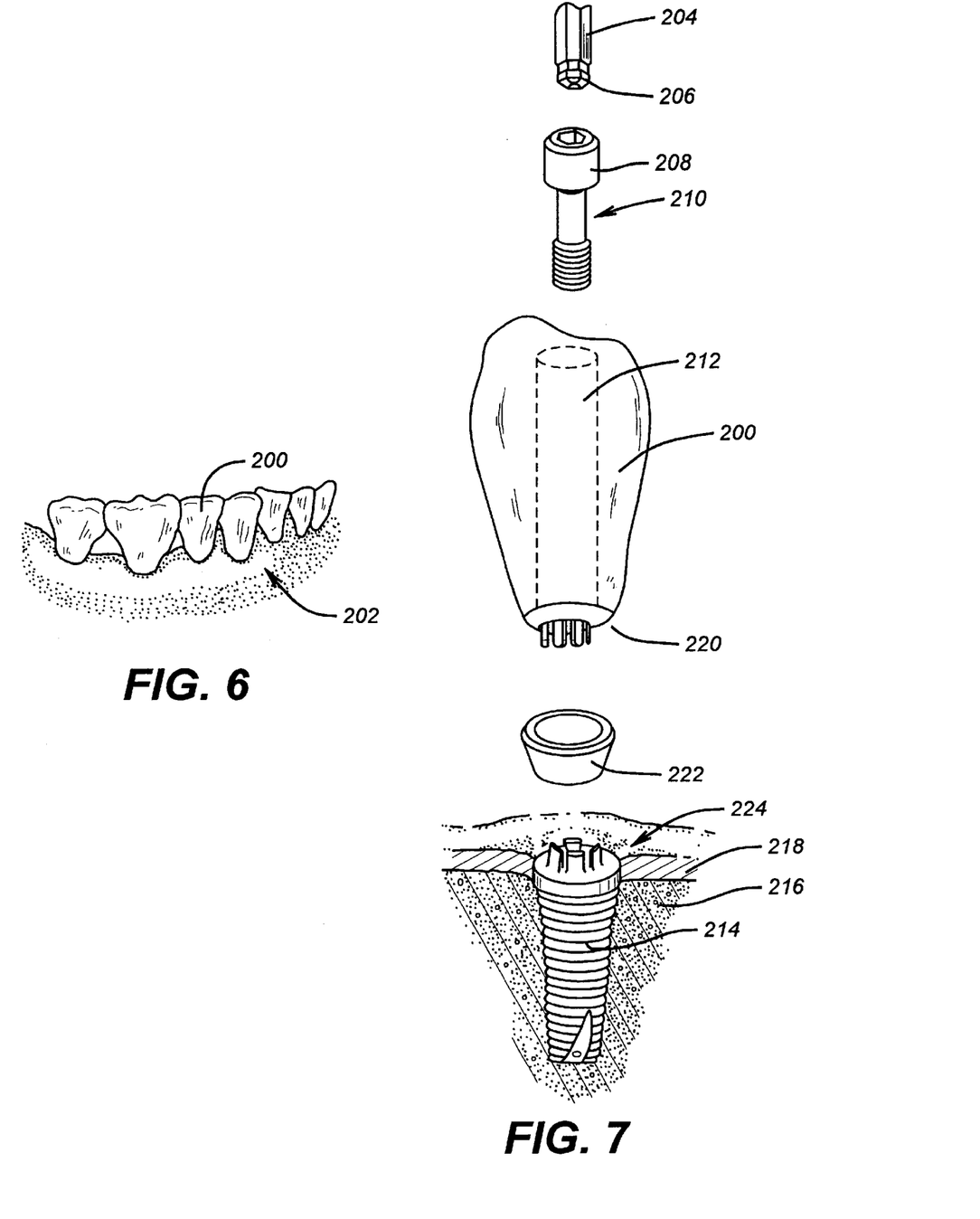
FIG. 6 is a partial view of a completely restored dental prosthesis.
FIG. 7 is an exploded view of the prosthesis and abutment of FIG. 6.

FIG. 6 shows a partial view of a patient's mouth having a retrievable dental prosthesis 200 embedded in jawbone 202. As shown in FIG. 7, a dental tool 204 is used to detach the prosthesis (connection of the abutment to the implant is more fully discussed in connection with FIGS. 2 and 3). This tool has an end 206 that engages the head 208 of screw 210. The tool passes into a cavity 212 in the prosthesis to access the screw. After the screw is loosened and removed from cavity 212, the prosthesis freely detaches from the implant 214. The implant remains embedded in the bone 216, and the surrounding soft tissue 218 remains unaffected.

FIG. 7 shows that the upper portion 220 remains attached to the prosthesis. The cuff 222, however, is not permanently attached to the prosthesis or implant. As such, the next step is to separate the cuff from the upper portion.

The cuff may be connected to the upper portion in various ways. FIG. 2, for example, shows that the cuff and upper portion are threaded together. Alternatively, the cuff could be press fit to the upper portion or connected in other ways known to those skilled in the art. Regardless of the fit between the cuff and the upper portion, the two pieces preferably can be separated.

At this point, the cuff may be replaced. The old cuff may, for example, be damaged or scratched and need to be replaced with a new one. Alternatively, a cuff having a different shape, size, coating, or composition, as discussed herein, may be preferred to the old cuff. For example, a new cuff having a porcelain coating could replace the old cuff. This new cuff would provide aesthetic advantages for the patient. As another example, the new cuff could have a different size to accommodate for receding tissue around the prosthesis. In general, the new cuff should be selected to accommodate the particular needs of the patient and could have any one of various designs discussed herein.

The next step is to place the new cuff back on the gingival end 224 of the implant. Thereafter, the prosthesis is placed on the cuff such that the upper portion and cuff connect to form an assembled abutment. The screw 210 is then positioned back into cavity 212 and passed through the abutment to engage the implant. The noted dental tool 204 passes into the cavity to engage and tighten the screw.

One advantage of the present invention is that the cuff of the abutment may be changed without altering or affecting the prosthesis. With prior unitary abutments, the cuff cannot be removed from the upper portion. As such, in order to change the cuff, the entire abutment has to be replaced. In this instance, a new prosthesis may also need to be fabricated to the new upper portion of the abutment. Fabricating a second prosthesis would be time consuming and costly.

In the present invention, after the prosthesis is removed, a new cuff is placed on the implant and the prosthesis is re-attached. The prosthesis itself though did not have to be modified or replaced. Thus, a second prosthesis does not have to be fabricated. Further, the procedure to replace the cuff is relatively quick and not invasive to the patient. Further yet, no additional costs are necessary to replace the entire abutment since the original upper portion may be used even after a new cuff is placed on the implant.

Figure 8:
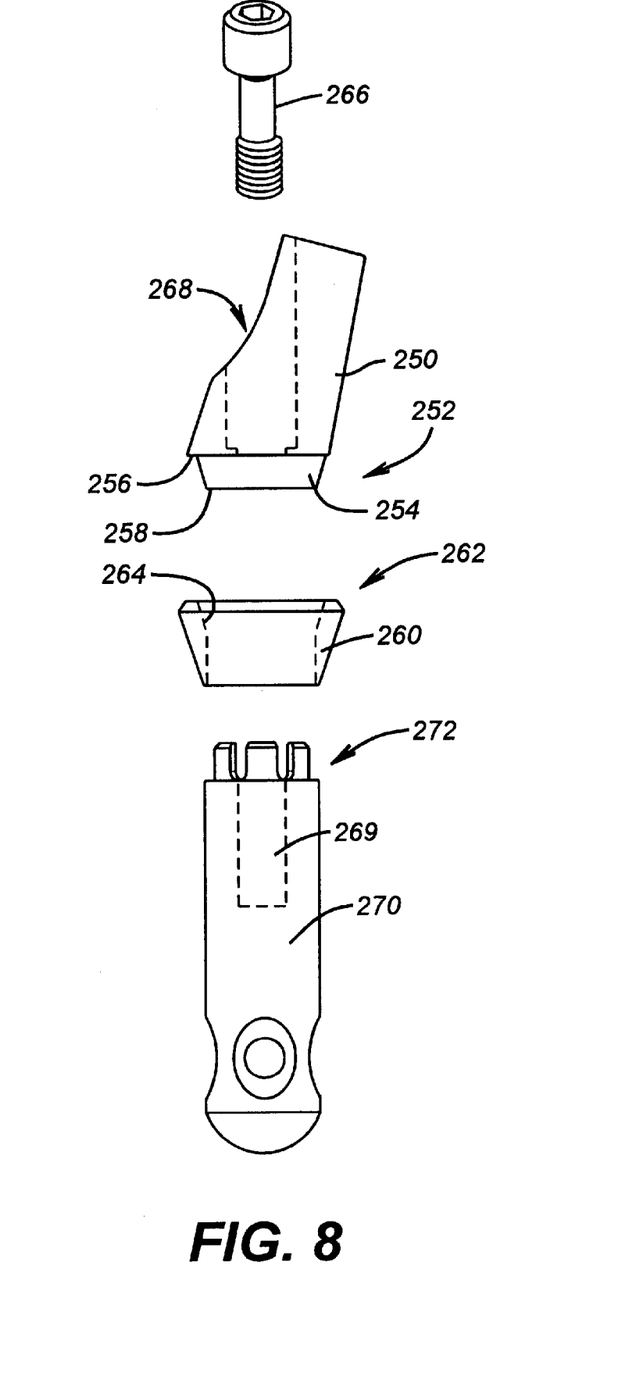
FIG. 8 is an exploded view of a dental implant and an alternate two-piece dental abutment according to the present invention.

Other variations of the abutment are also within the scope of this invention. FIG. 8 shows one such alternate embodiment. Here, the upper portion 250 has a base 252 that includes a cylindrical extension 254. This extension tapers from a shoulder 256 to an end 258.

The cuff 260 has a top portion 262 with a tapering, cylindrical cavity or recess 264. This cavity is sized and shaped to fit together with the extension 254. When the abutment is assembled, the upper portion fits on top of the cuff with the extension within the cavity. A screw 266 passes through a bore 268 in the abutment and into a threaded cavity 269 in the implant 270. This screw holds the abutment to the implant and also prevents the upper portion from rotating about the cuff. The cuff may be provided with splines (not shown) or another engaging feature to prevent rotation between the cuff and implant.

One advantage of the abutment shown in FIG. 8 is that the upper portion and cuff may be rotated to numerous positions relative to each other. Once the cuff is positioned on the gingival end 272 of the implant, the upper portion may be rotated 360° about the longitudinal axis running through the implant and cuff. Once the proper orientation of the upper portion is determined, the screw 266 is tightened to hold the upper portion in place and prevent relative movement between the cuff and the upper portion.

Figure 9:
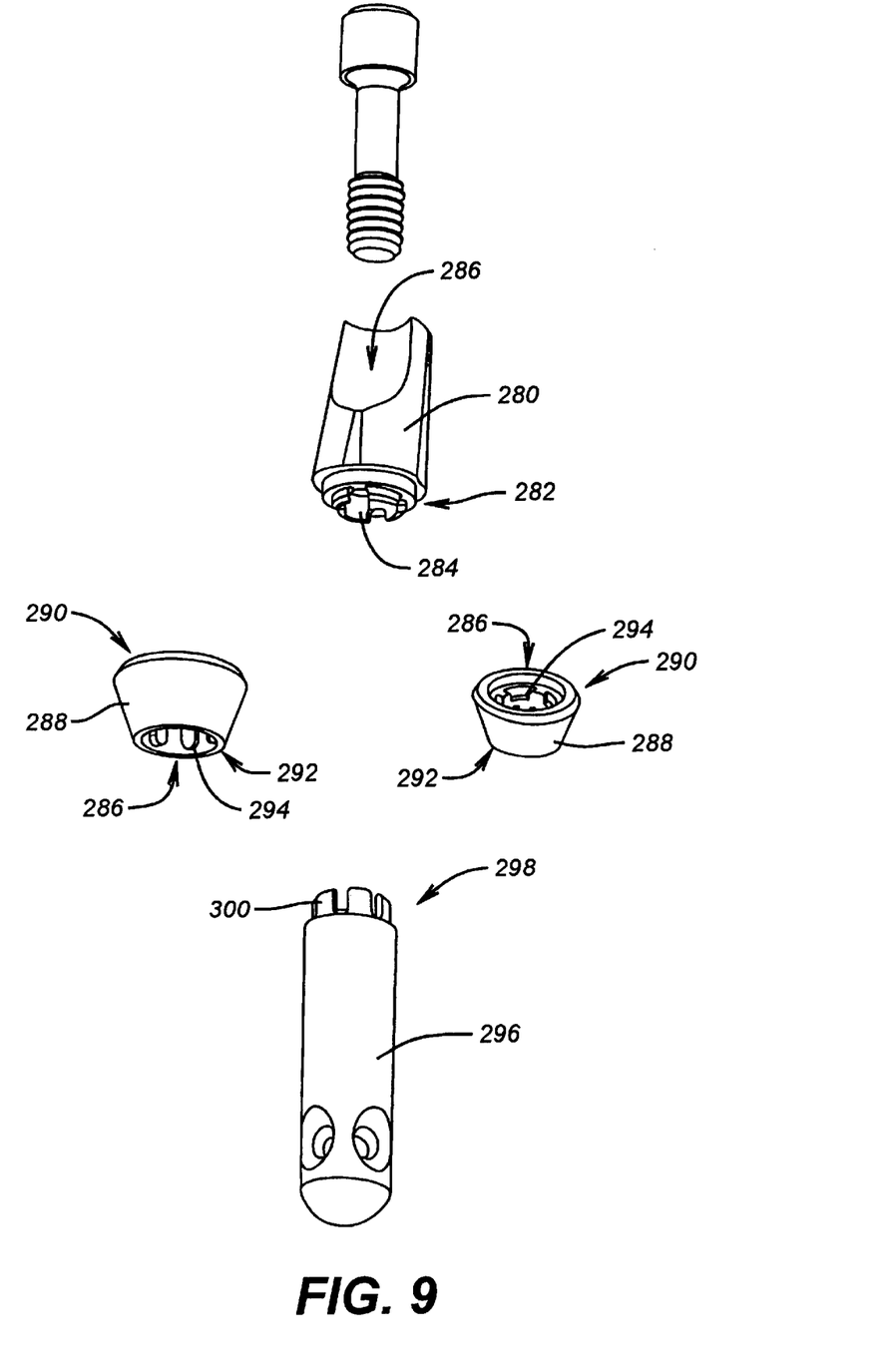
FIG. 9 is an exploded view of a dental implant and an another alternate two-piece dental abutment according to the present invention.

FIG. 9 depicts another alternate embodiment. Here, the upper portion 280 has a base 282 that includes an engaging feature 284. This engaging feature comprises four tines extending downwardly. A cylindrical bore 286 extends through the upper portion 280 and cuff 288.

Two different perspective views of the same cuff 288 are shown. The cuff has a top portion 290 and a support surface 292. An engaging feature 294 extends along the bore 286 from the top portion 290 to the support surface 292. This engaging feature is comprised of Spline™ tine receptors. These receptors enable the cuff to engage both the upper portion and implant 296. The use of tines on the upper and lower engaging portions provides double indexing.

The gingival end 298 of the implant includes a plurality of tines 300. These tines engage the tine receptors when the support surface 292 of the cuff is positioned on the gingival end of the implant.

The cuff may be rotated between several positions at various intervals depending on the number of tines. Likewise, when the base 282 of the upper portion is positioned on the top portion 290 of the cuff, the upper portion may be rotated relative to the cuff. Rotation of the cuff relative to the implant and upper portion relative to the cuff provides the noted double indexing.

Other engaging features, besides tines, may be used for any of the embodiments shown in the figures. For example, the upper portion and the cuff could include polygonal engaging features. The base portion of the upper portion could have a hexagonal projection, and the engaging feature in the bore of the cuff could be a hexagonal female receptor. Further to this end, the gingival end of the implant could have a polygonal engagement, such as a hexagonal projection. Of course, the male and female engaging features for all embodiments within the scope of this invention may be switched between the upper portion, cuff, and implant.

Figure 10A:
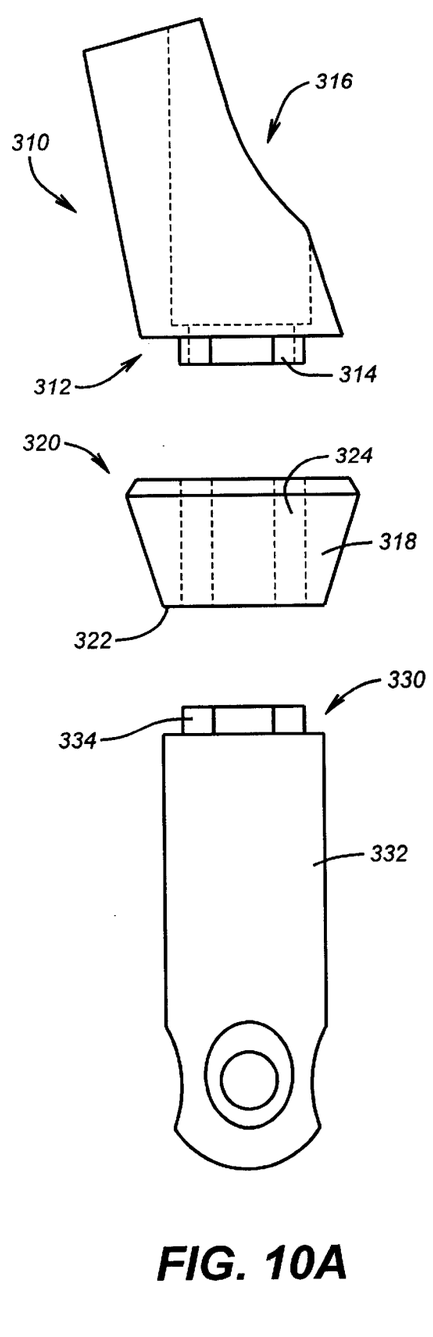
FIG. 10A is an exploded view of a dental implant and yet another alternate two-piece dental abutment according to the present invention.
Figure 10B:
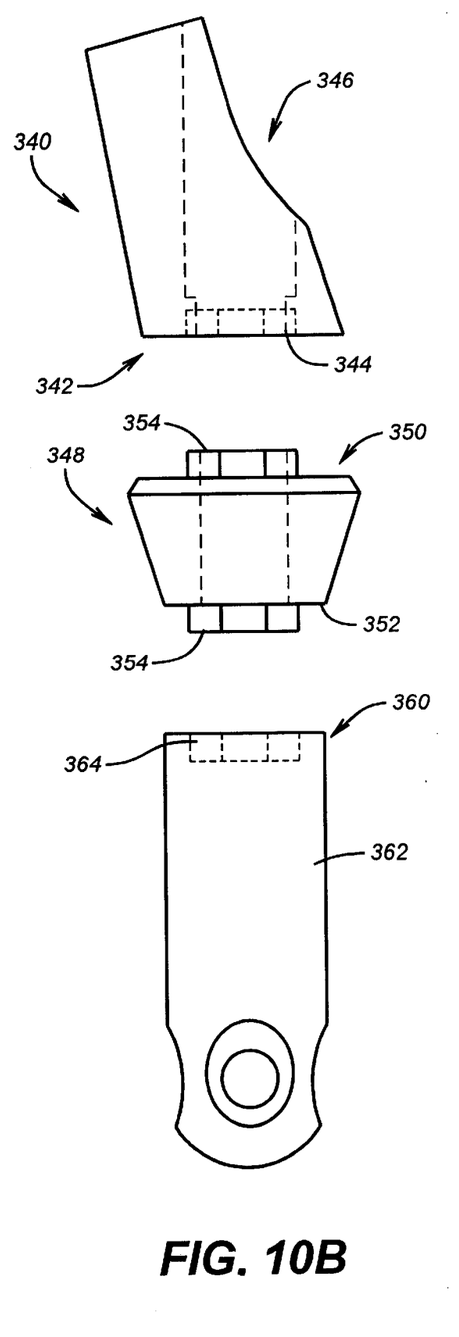
FIG. 10B is an exploded view of a dental implant and yet another alternate two-piece dental abutment according to the present invention.

FIGS. 10A and 10B show example embodiments using polygonal engaging features. In FIG. 10A, the upper portion 310 has a base 312 that includes an engaging feature 314. This engaging feature comprises a hexagonal projection. A bore 316 extends through the upper portion 310 and cuff 318.

The cuff 318 has a top portion 320 and a support surface 322. An engaging feature 324 extends along the bore 316 from the top portion 320 to the support surface 322. This engaging feature comprises a hexagonally shaped bore.

The gingival end 330 of the implant 332 includes an engaging feature 334 formed as a hexagonal projection. This projection engages the hexagonal bore 324 when the support surface 322 of the cuff is positioned on the gingival end of the implant.

In FIG. 10B, the upper portion 340 has a base 342 that includes an engaging feature 344. This engaging feature comprises an octagonal recess. A bore 346 extends through the upper portion 340 and cuff 348.

The cuff 348 has a top portion 350 and a support surface 352. An engaging feature 354 projects outwardly from the support surface and from the top portion. This engaging feature comprises an octagonally shaped projection.

The gingival end 360 of the implant 362 includes an engaging feature 364 formed as a hexagonal recess. This projection engages the hexagonal projection 354 when the support surface 352 of the cuff is positioned on the gingival end of the implant.

In FIGS. 10A and 10B, the cuff may be rotated between several positions with respect to the implant. Likewise, when the base of the upper portion is positioned on the top portion of the cuff, the upper portion may be rotated relative to the cuff. As in FIG. 9, this dual rotation may provide the noted double indexing if the polygons have different geometric configurations.

Figure 11:
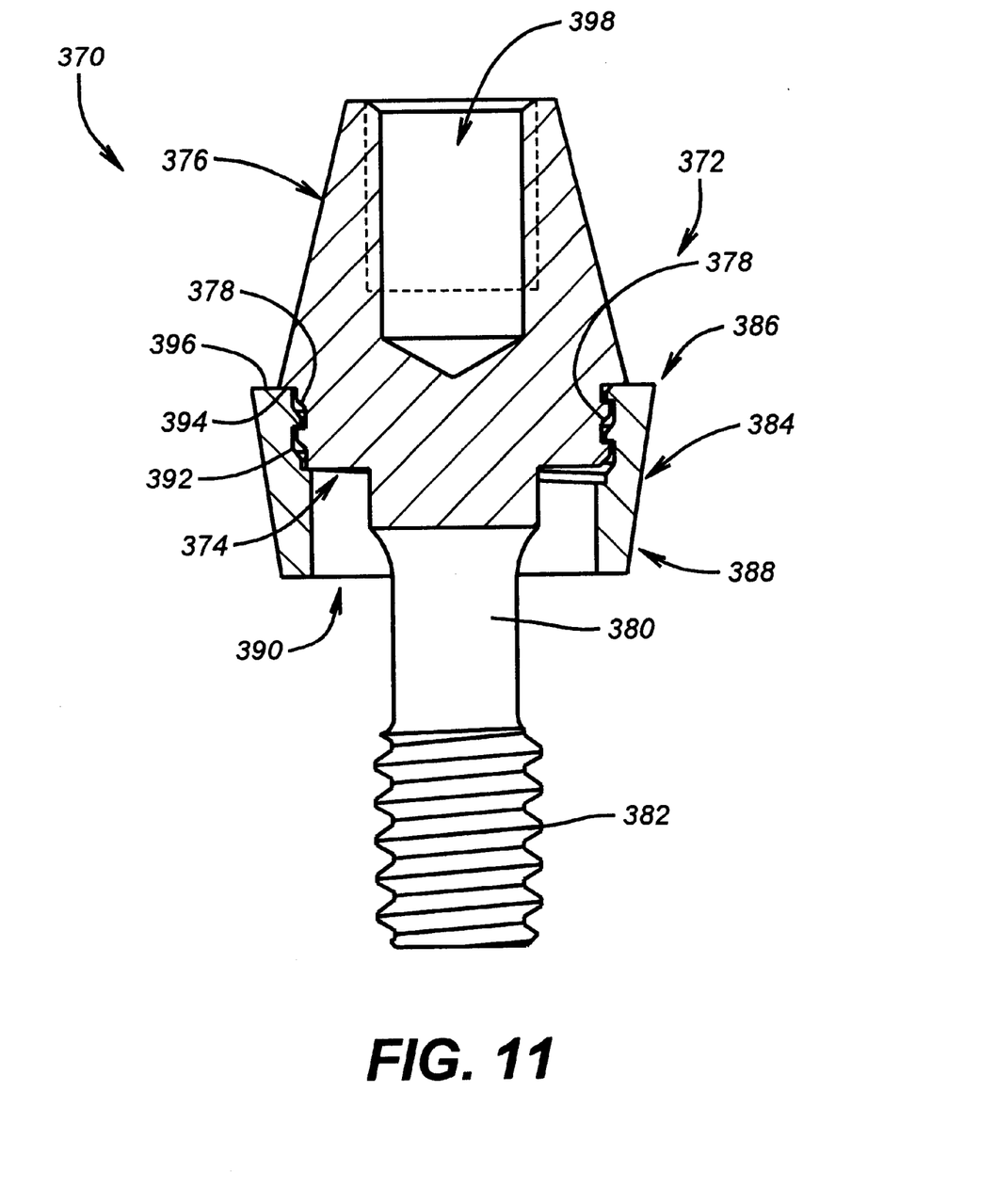
FIG. 11 is a partial cross sectional view of yet another alternate two-piece dental abutment according to the present invention.

FIG. 11 shows an example embodiment of another two-piece abutment 370 according to the invention. The upper portion 372 has a base 374 and a top portion 376. The base includes a threaded exterior surface 378 and a shaft 380 extending downwardly from the threaded surface 378. This shaft includes a threaded section 382.

The cuff 384 has a top portion 386 and a bottom portion 388. A passageway 390 extends through the cuff and has a threaded interior portion 392 that threads with the threaded surface 378 on the upper portion.

When the abutment is assembled, the shaft 380 extends through the passageway 390 until a shoulder 394 above the threaded surface 378 abuts with a top end 396 of the top portion 386. The threads 382 on the shaft 380 engage with a threaded bore at the gingival end of an implant (not shown). A separate screw to connect the abutment to the implant is thus not needed. A prosthesis (not shown) connects around the top portion 376 of the upper portion 372 and a screw (not shown) threads into the recess 398 to hold the prosthesis to the upper portion.

Figure 12A:
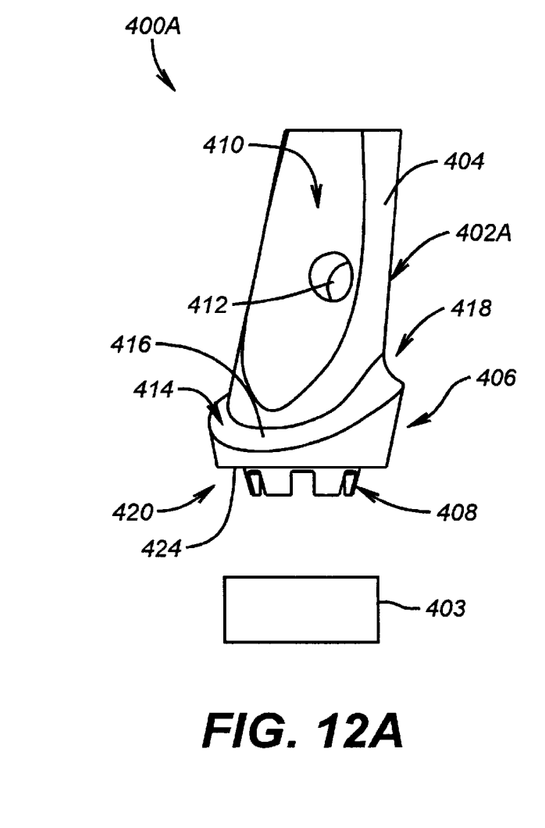
FIG. 12A is an exploded view of another alternate two-piece abutment.
Figure 12B:
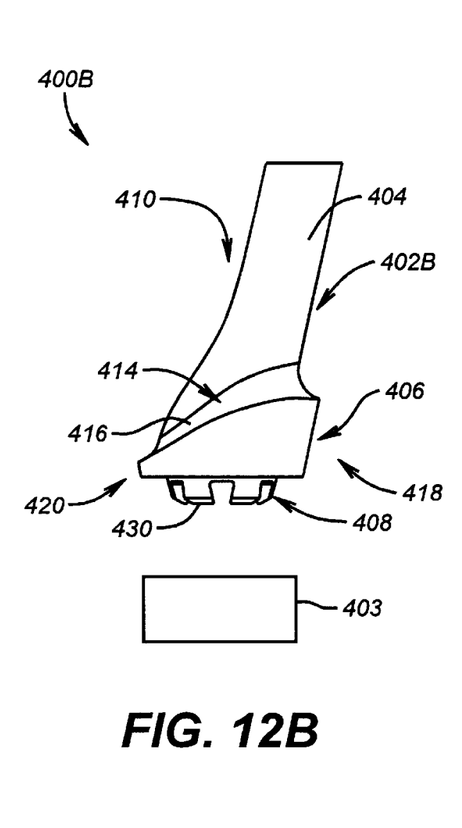
FIG. 12B is an exploded view of another alternate two-piece abutment.
Figure 12C:
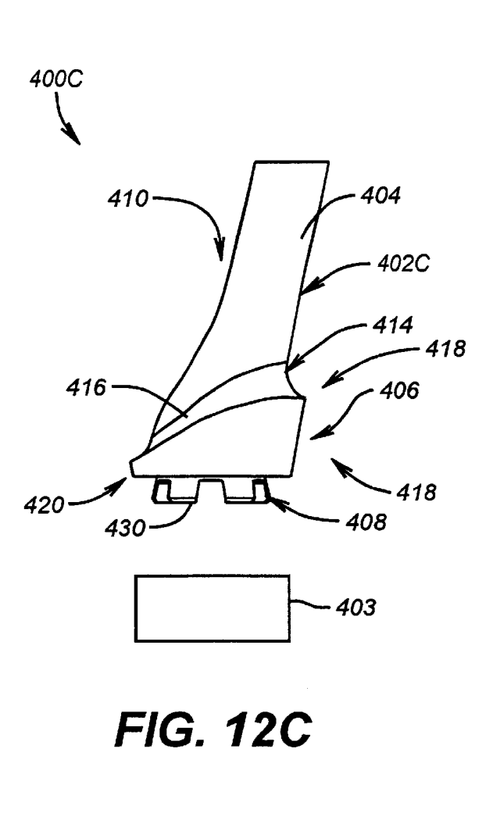
FIG. 12C is an exploded view of another alternate two-piece abutment.

Turning now to FIGS. 12A, 12B, and 12C, three more embodiments for the present invention are shown. Here, abutments 400A, 400B, and 400C each have an upper portion 402A, 402B, and 402C, respectively, and a cuff 403. Each upper portion has a top portion 404 and a base 406 that includes an engaging feature 408. This engaging feature comprises six tines extending downwardly. A bore 410 extends through the top portion 404 and cuff 403, and upper portion 402A (FIG. 12A) is shown having a second bore 412 through the side of the top portion for receiving a lingual screw (not shown). As shown, the base may taper slightly outwardly, and the top portion may taper slightly inwardly.

A transition region 414 extends between the base 406 and the top portion 404. This transition region includes a curved, smooth lip or margin 416. The margin extends circumferentially around the exterior of the upper portion and functions, in part, to support a prosthetic restoration (not shown).

Figure 13:
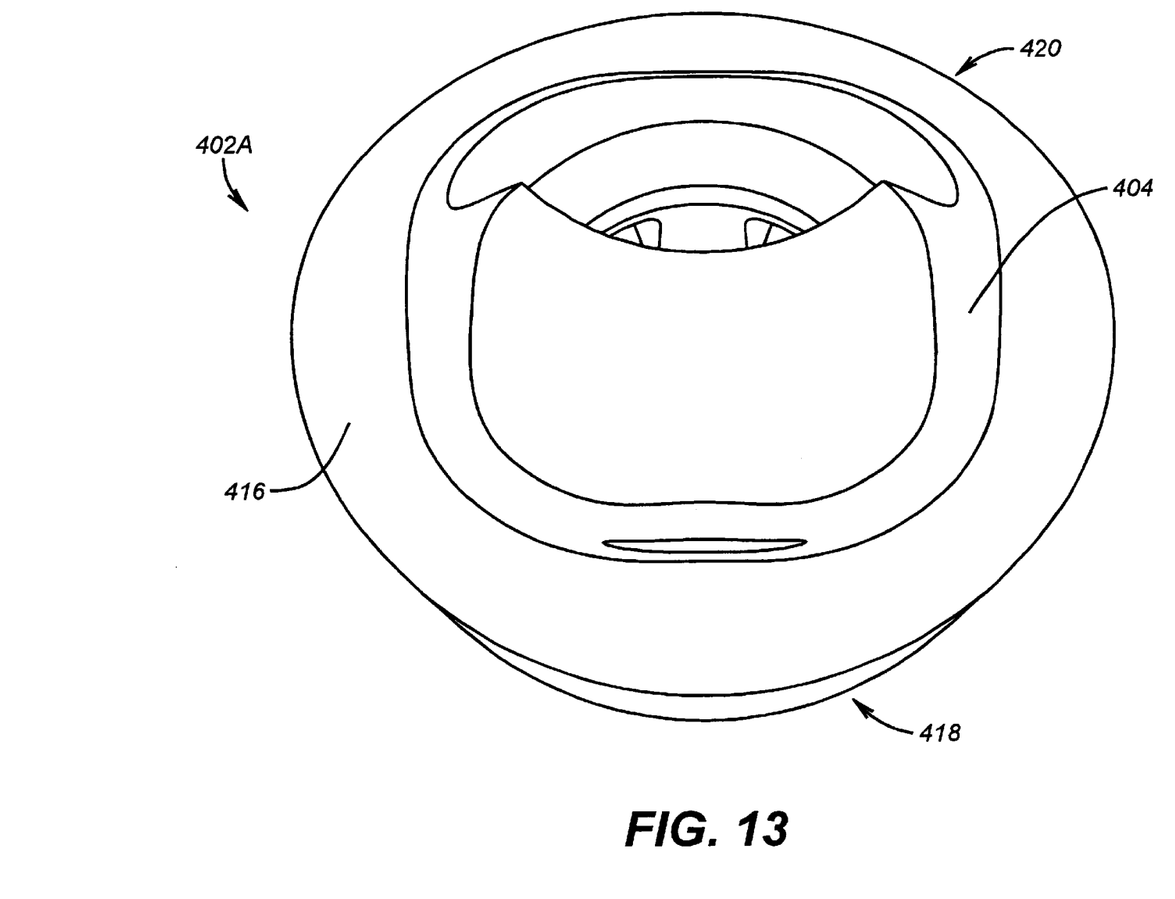
FIG. 13 is a top view of the upper portion of FIG. 12A.

One important advantage of this margin is that it has a contour that slopes downwardly from a back side 418 of the upper portion toward a front side 420 of the upper portion. As another advantage, the curvature or the margin around the upper portion more naturally follows the anatomical contour of a natural tooth. Further the slope more closely conforms with the natural, anatomical contour of the gingival tissue. FIG. 13 shows a top view of the upper portion 402A to better illustrate this curvature. As shown in this figure, margin 416 has a noncircular curvature and may be, for example, elliptical or a tapered rectangular prism with radius corners.

Turning now to specific attributes of the engaging feature 408. In FIG. 12A, the individual tines of upper portion 402A are tapered. As shown, the thickness of these tines decreases as the tines extend downwardly from a bottom surface 424.

Looking now to FIG. 12B, the thickness of the tines is constant. The tines, however, are bent inwardly toward the center of bore 410. Preferably, the tines are bent inwardly at an angle of up to about 15°. The distance between adjacent tines will decrease slightly after the tines are bent inwardly. The tines may also be bent outwardly, as shown in FIG. 12C. Chamfer 430 at the bottom of all bent tines terminates in a shape and size sufficiently small to engage the upper opening in cuff 403. Preferably, the tines are bent outward at an angle of up to about 15°.

The cuff 403 in FIGS. 12A, 12B, and 12C is very similar to the cuff 288 described in connection with FIG. 9. One difference, though, is that cuff 403 has six Spline™ tine receptors to receive the corresponding six tines of the engaging feature 408. Another difference is that the cuff has a cylindrical configuration that is not tapered.

When the engaging feature 408 of each upper portion 402A, 402B, and 402C is placed into the bore of the cuff 403, the tines of the upper portion engage the six tine receptors. This engagement forms a frictional fit between the upper portion and the cuff. The upper portion and the cuff are thus held together, but they may thereafter be separated if a pulling force is applied between them.

FIG. 12A shows an engaging feature 408 that includes tines. Other types of engaging features may be used instead of tines. For example, a polygonal projection (such as a hexagon or octagon) could extend downwardly from surface 424. The sides of the polygonal feature could be tapered inwardly and engage a corresponding polygonal recess in the cuff 403.

The invention claimed is:

1. A two-piece dental abutment, comprising:
   an upper portion formed entirely from a first material and having a base portion with a first engaging feature that extends downwardly therefrom; and
   a cuff formed from a second material different than the first material and having a bore extending centrally through the cuff, and a second engaging feature that engages the first engaging feature to provide anti-rotational engagement between the cuff and the upper portion.

2. The dental abutment of claim 1 in which the first and second engaging features frictionally engage together.

3. The dental abutment of claim 1 in which:
   the base portion has a bottom surface; the first engaging feature extends downwardly from this bottom surface; and
   the thickness of the first engaging feature decreases as it extends from the bottom surface.

4. The dental abutment of claim 1 in which:
   the base portion has a bottom surface; and
   the first engaging feature includes a plurality of tines that extend downwardly from this bottom surface.

5. The dental abutment of claim 4 in which the tines are bent.

6. The dental abutment of claim 4 in which at least one tine is bent inwardly at an angle of up to about 15°.

7. The dental abutment of claim 4 in which at least one tine is bent outwardly at an angle of up to about 15°.

8. The dental abutment of claim 4 in which the tines taper.

9. The dental abutment of claim 4 in which the tines have a thickness that decreases as the tines extend away from the bottom surface.

10. The dental abutment of claim 1 in which the upper portion has a top portion and a transition portion between the top portion and the base portion.

11. The dental abutment of claim 10 in which the transition region has an anatomical configuration.

12. The dental abutment of claim 10 in which the transition region includes a margin that curves around the upper portion.

13. The dental abutment of claim 12 in which the margin slopes downwardly from a back portion of the upper portion to a front portion of the upper portion.

14. The dental abutment of claim 13 in which the margin has an elliptical configuration.

15. A two-piece dental abutment that connects a dental prosthesis to an implant with an engaging feature of a plurality of male tines at its gingival end, the abutment comprising:
   a first piece having a lower end with a base having an engaging feature of a plurality of male tines, a top portion extending above the base for attaching to the dental prosthesis, a bore extending through the top portion and base, and a shoulder in the bore to abut a screw;
   a second piece connectable to the first piece and having a lower end and a top end, a bore extending through the second piece from the top end to lower end, and an engaging feature of a plurality of female tine receptors in the bore and located at both the top end and lower end;
   the lower end of the second piece abutting the gingival end of the implant so the engaging feature of the implant engages the engaging feature of the second piece; and
   the top end of the second piece frictionally engaging the lower end of the first piece so the bore in the first piece aligns with the bore in the second piece.

16. The abutment of claim 15 in which the male tines of the first piece taper.

17. The abutment of claim 15 in which at least one of the male tines of the first piece are bent inwardly.

18. The abutment of claim 15 in which at least one of the male tines of the first piece are bent outwardly.

19. The abutment of claim 15 in which the top portion of the first piece forms an acute angle with respect to the bore of the second piece.

20. The abutment of claim 19 in which the angle ranges from 5° to 45°.

21. The abutment of claim 15 in which the first piece has a transition region that extends between the base and the top portion.

22. The abutment of claim 21 in which the transition region is elliptical.

23. The abutment of claim 21 in which the transition region has an anatomical configuration.

24. The abutment of claim 21 in which the transition region has a margin that slopes downwardly from a back portion of the top portion to a front portion of the top portion.

25. The abutment of claim 21 in which the transition region has a margin that has a non-circular curvature.

26. The abutment of claim 21 in which the transition region has a margin that has smooth curved configuration that extends around the top portion.

27. A multi-piece dental abutment for attaching a prosthesis to an implant, comprising:
   a first piece having a base portion and a top portion, a bore extending through the base and top portions, and a first engaging feature extending from the base portion;
   a second piece having a lower end and an upper end, a bore extending through second piece from the lower end to the upper end, and a second engaging feature;
   the second engaging feature engaging the first engaging feature when the base of the first piece abuts the upper end of the second piece; and
   the top portion of the first piece forms an angle with respect to the bore of the second piece, and the first and second piece are made from different materials.

28. The dental abutment of claim 27 in which the first and second engaging features frictionally engage each other.

29. The dental abutment of claim 28 in which the first and second piece may be removed from each other after the first and second engaging features engage each other.

30. The dental abutment of claim 27 in which the first piece has a lip that extends between the top portion and base portion.

31. The dental abutment of claim 30 in which the lip has an anatomical configuration.

32. The dental abutment of claim 30 in which the lip has a smooth curvature that slopes downwardly.

33. A dental abutment for connecting a dental prosthesis to a dental implant, the abutment comprising:
- two separate and different pieces, including a first piece and a second piece;
- the first piece being made entirely from a first material and having a first bore extending therethrough and having a polygonal projection extending downwardly from one end;
- the second piece being made from a second material different than the first material and having a body with a polygonal bore extending therethrough;
- the polygonal projection fitting into the polygonal bore to provide anti-rotational engagement between the first and second pieces;
- the first piece connecting to the prosthesis; and
- the second piece connecting to the implant.

34. The abutment of claim 33 in which the polygonal bore and polygonal projection are shaped as hexagons.

35. The abutment of claim 33 in which the second piece has a straight cylindrical configuration.

36. The abutment of claim 33 in which the first piece has an anatomical configuration.

37. The abutment of claim 36 which the anatomical configuration is non-circular and slopes.

38. The abutment of claim 36 in which the anatomical configuration is elliptical.

39. The abutment of claim 33 in which the first piece has a base that tapers outwardly and a top portion that tapers inwardly.

40. The abutment of claim 33 in which a lip extends between the base and the top portion, and the lip has a non circular shape.

41. The dental abutment of claim 33 in which the second piece has a porcelain coating.

* * * * *